the tip. Ventral edge—thick, many small ridges and usually one large groove on each side. Dorsal edge—two ridges with a groove between many times continuous except as it approaches the tip, other times interrupted. Dorsal ridges broken and irregular near the tip, in practically all cases.

*Color.*—Dark brown and tinged with some red (7–E–11).

Use: Market, local, dessert, culinary, long distance shipping.

Keeping quality: Good.

*General notes*

The tree and its fruit herein described may vary some due to climatic and soil conditions under which the variety may be grown, and the method of growing, including fertilizing, pruning, thinning, the pests and diseases present on the tree and other causes.

The following is claimed:

A new and distinct variety of peach tree substantially as described and illustrated, characterized particularly as to novelty, by a late ripening period, about five days later than Merrill Splendor (Plant Patent No. 1,257) and twenty five days later than Elberta (unpatented), by its late blooming period, about five days later than Merril Splendor (Plant Patent No. 1,257) and about ten days later than Redhaven (unpatented), and being similar to Merril Splendor (Plant Patent No. 1,257) in its fruit and tree characteristics, being an improvement on that variety because of its later blooming and ripening date as specified above and additionally having a redder skin color.

No references cited.